US006986759B1

(12) United States Patent
Jeremijevic

(10) Patent No.: US 6,986,759 B1
(45) Date of Patent: Jan. 17, 2006

(54) DEVICE FOR PROTECTING AND NEUTRALIZING A NEEDLE FOR MEDICAL USE

(75) Inventor: Vojin Jeremijevic, Montreuil-sous-Bois (FR)

(73) Assignee: Device Research & Development (DRD), Grand Duche de Luxembourg (LU)

( * ) Notice: Subject to any disclaimer, the term of this patent is extended or adjusted under 35 U.S.C. 154(b) by 0 days.

(21) Appl. No.: 09/674,643

(22) PCT Filed: May 7, 1999

(86) PCT No.: PCT/FR99/01083

§ 371 (c)(1),
(2), (4) Date: Nov. 2, 2000

(87) PCT Pub. No.: WO99/59660

PCT Pub. Date: Nov. 25, 1999

(30) Foreign Application Priority Data

| May 15, 1998 | (FR) | ................................... 98 06277 |
| Dec. 30, 1998 | (FR) | ................................... 98 16701 |
| Feb. 4, 1999 | (FR) | ................................... 99 01284 |

(51) Int. Cl.
*A61M 5/32* (2006.01)
*A61M 5/00* (2006.01)

(52) U.S. Cl. ...................... 604/198; 604/192; 604/110; 604/263

(58) Field of Classification Search ............... 604/263, 604/110–198, 264; 600/573, 584; 435/810
See application file for complete search history.

(56) References Cited

U.S. PATENT DOCUMENTS

| 4,283,498 A | * | 8/1981 | Schlesinger ................. 435/810 |
| 4,790,828 A | * | 12/1988 | Dombrowski et al. ...... 604/110 |
| 5,197,954 A | * | 3/1993 | Cameron ..................... 128/919 |
| 5,304,151 A | * | 4/1994 | Kuracina ..................... 604/198 |
| 5,743,888 A | * | 4/1998 | Wilkes et al. ............... 604/192 |
| 5,925,020 A | * | 7/1999 | Nestell ....................... 604/198 |
| 6,443,929 B1 | * | 9/2002 | Kuracina et al. ........... 604/192 |

* cited by examiner

Primary Examiner—Nicholas D. Lucchesi
Assistant Examiner—Roz Maiorino
(74) Attorney, Agent, or Firm—Sughrue Mion, PLLC

(57) ABSTRACT

The invention relates to devices for protecting a needle 1 for medical use or the like and having a sharp end 2 and a base end 3. The device of the invention is essentially characterized by the fact that it comprises a sleeve 10 having a bore 11 on an axis 12 and of section not less than that of the needle to be protected, a link 13 of length "$L_1$", resilient return hinge means 19 for connecting one end 15 of the link 14 to the sleeve 10, the link taking up a defined equilibrium position on a direction making an acute angle α with the axis of the bore 11, base means 21 suitable for receiving the end 3 of the needle 1, a crank arm 22 of length "$K_1$" no greater than the length "$L_1$" of the link, and means 28, 30 for mounting each of the first and second ends of the crank arm 22 to pivot freely respectively on the end 17 of the link 13 and on the base means 21.

24 Claims, 7 Drawing Sheets

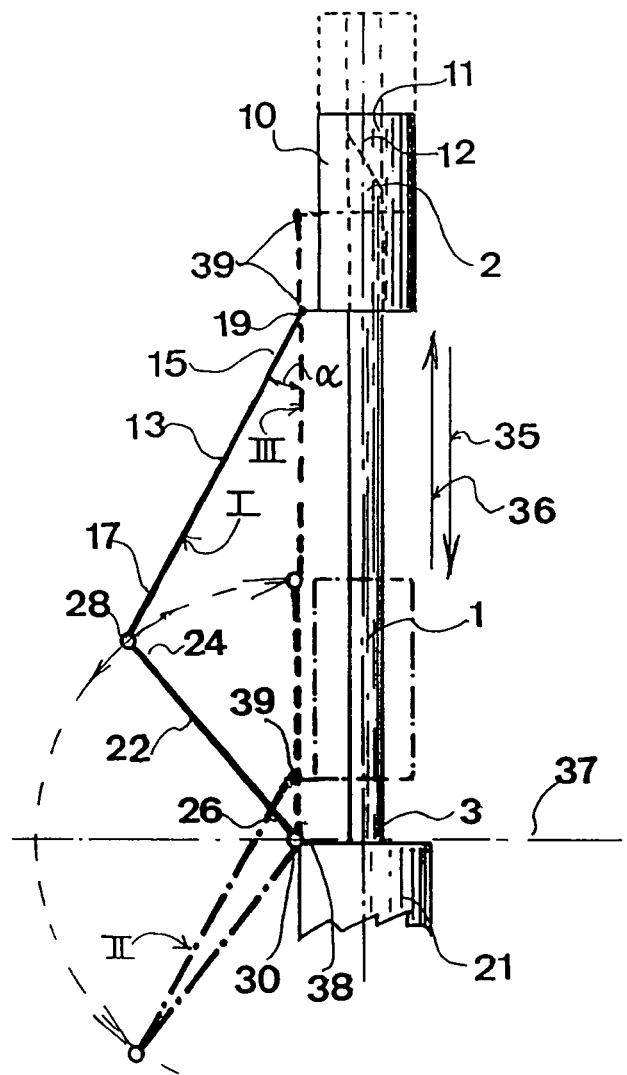
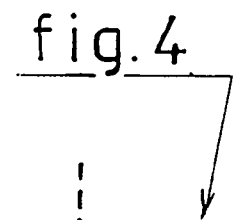
fig. 4
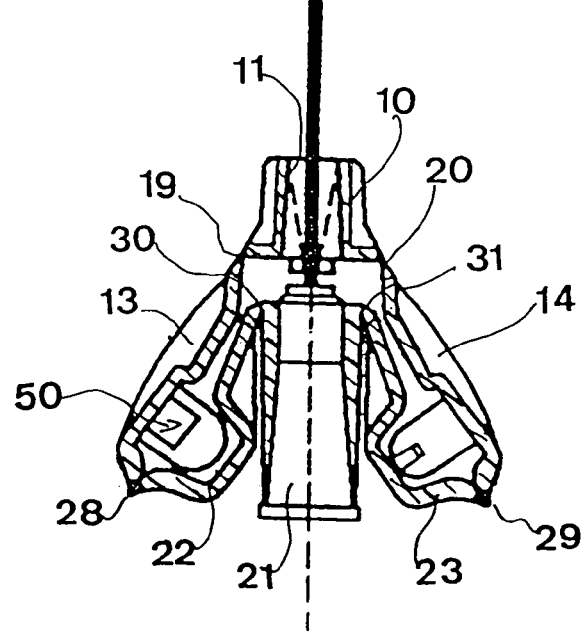

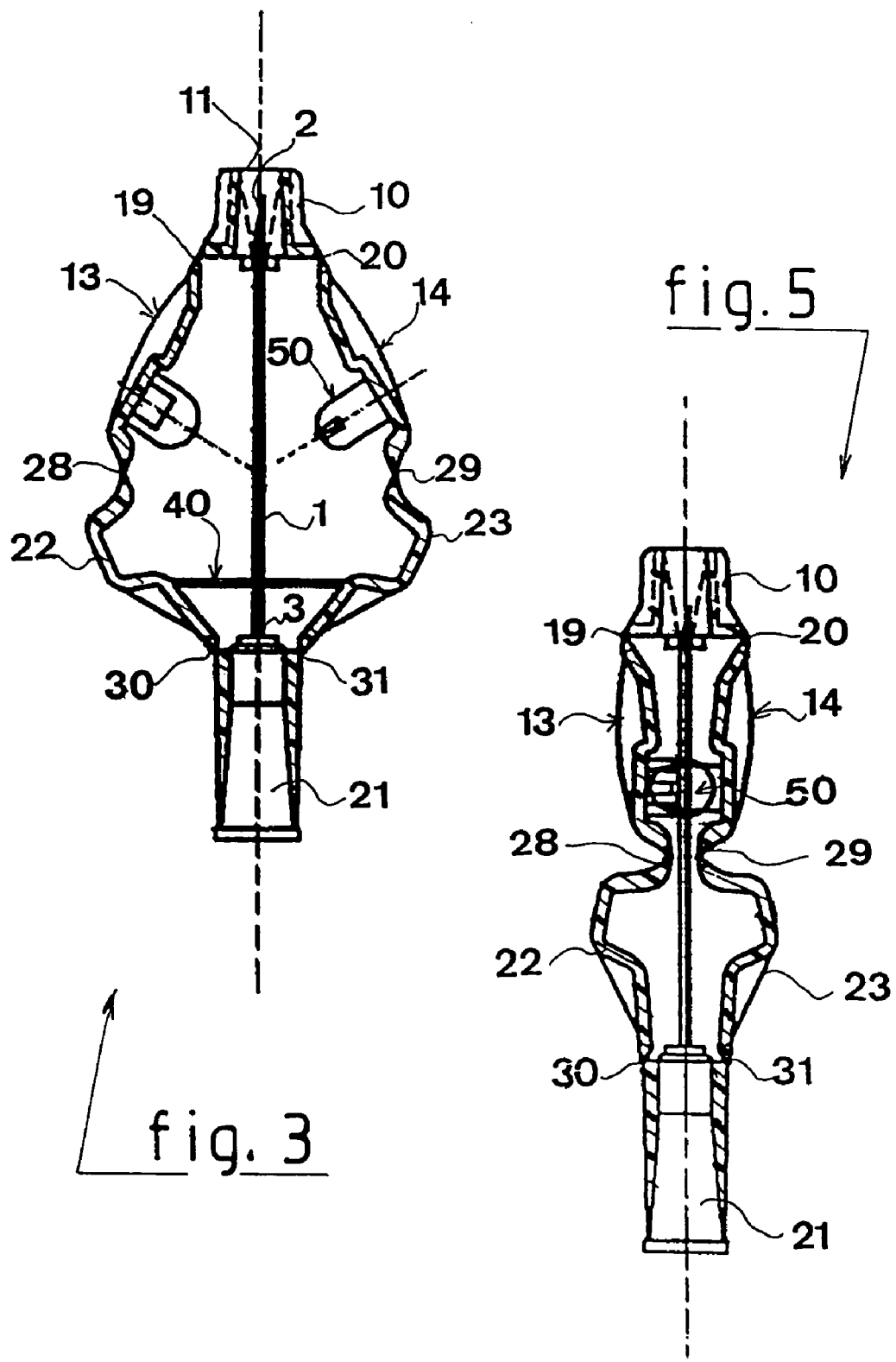

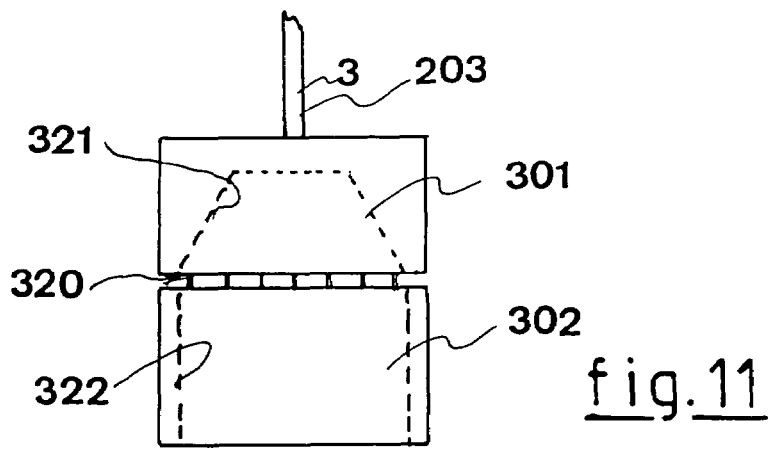
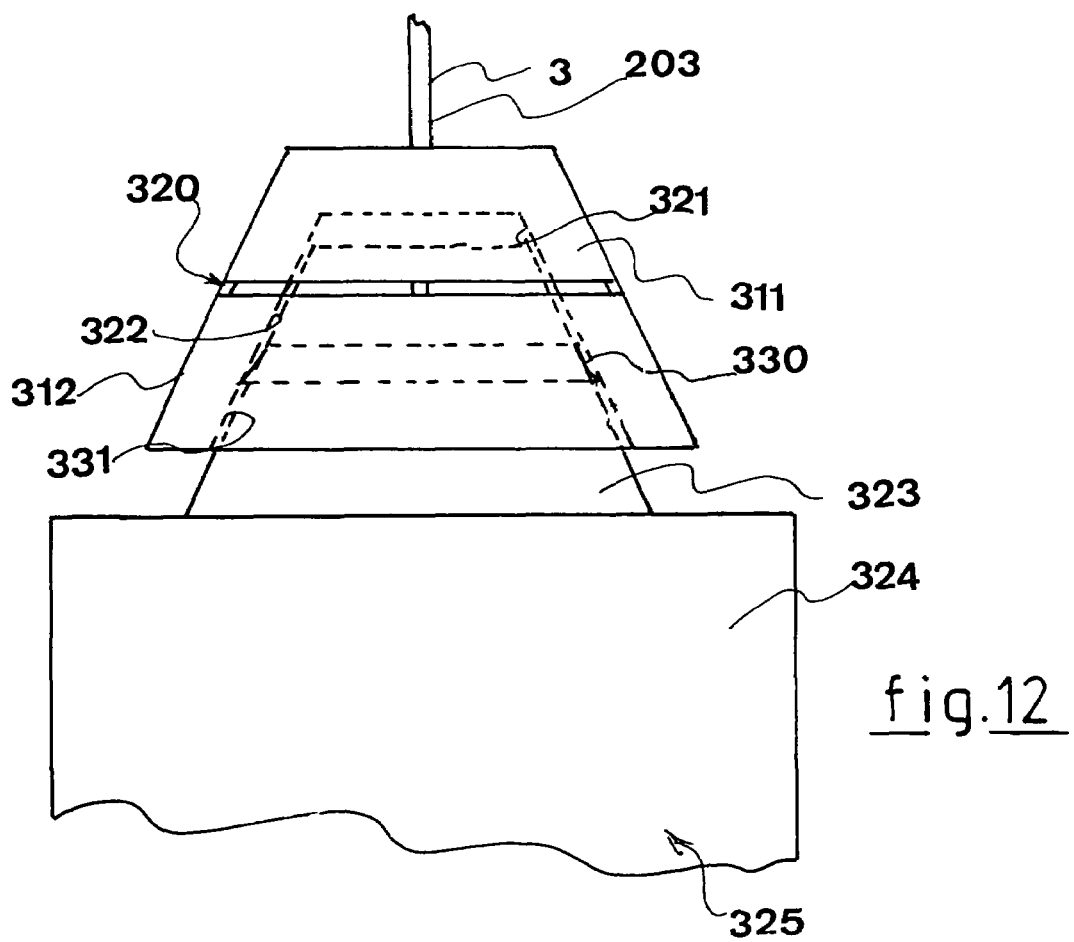

DEVICE FOR PROTECTING AND NEUTRALIZING A NEEDLE FOR MEDICAL USE

The present invention relates devices for protecting and neutralizing needles that have a sharp end and a base end, which have a particularly advantageous application lying specifically in protecting and neutralizing the needles of syringes, and more particularly devices for protecting and neutralizing needles that are intended for use by professionals in the medical field or the like.

Needle protection and neutralization devices already exist, but they are generally relatively complex and expensive, which limits their use.

Thus, a particular object of the present invention is to provide a device for protecting and neutralizing a needle for medical use or the like which greatly mitigates the drawbacks of prior art devices.

More precisely, the present invention provides a device for protecting and neutralizing a needle for medical use or the like, the needle having a sharp end and a base end, the device being characterized by the fact that it comprises:

- a sleeve having a through bore defined on a given axis, said through bore being of a section that is not less than that of the needle to be protected;
- at least one first link having first and second ends, said first link being of a defined length "$L_1$" between its two ends;
- first resilient return hinge means for connecting the first end of the first link to the sleeve, said first hinge means being organized so that said first link takes up a defined equilibrium position on a direction that makes an acute angle with the axis of the through bore;
- base means suitable for receiving the base end of the needle;
- at least one first crank arm defined between first and second ends, said first crank arm being of a defined length "$I_1$" between its two ends, the length "$I_1$" being no greater than the length "$L_1$" of the first link; and
- first means for mounting each of said first and second ends of the first crank arm to pivot freely respectively on the second end of the first link and on the base means.

Other characteristics and advantages of the present invention appear from the following description given with reference to the accompanying drawings by way of non-limiting illustration, and in which:

FIG. 1 is a theoretical diagram of the device of the invention for protecting and neutralizing a needle for medical use or the like;

FIGS. 3 to 5 are fragmentary longitudinal section views of the embodiment shown in FIG. 2, respectively in three positions in which the device of the invention can be found while it is being used, which positions are respectively referred to in the description below as the "starting position" (FIGS. 2 and 3), the "in-use position" (FIG. 4), and the "locked position" (FIG. 5);

Figure 6:
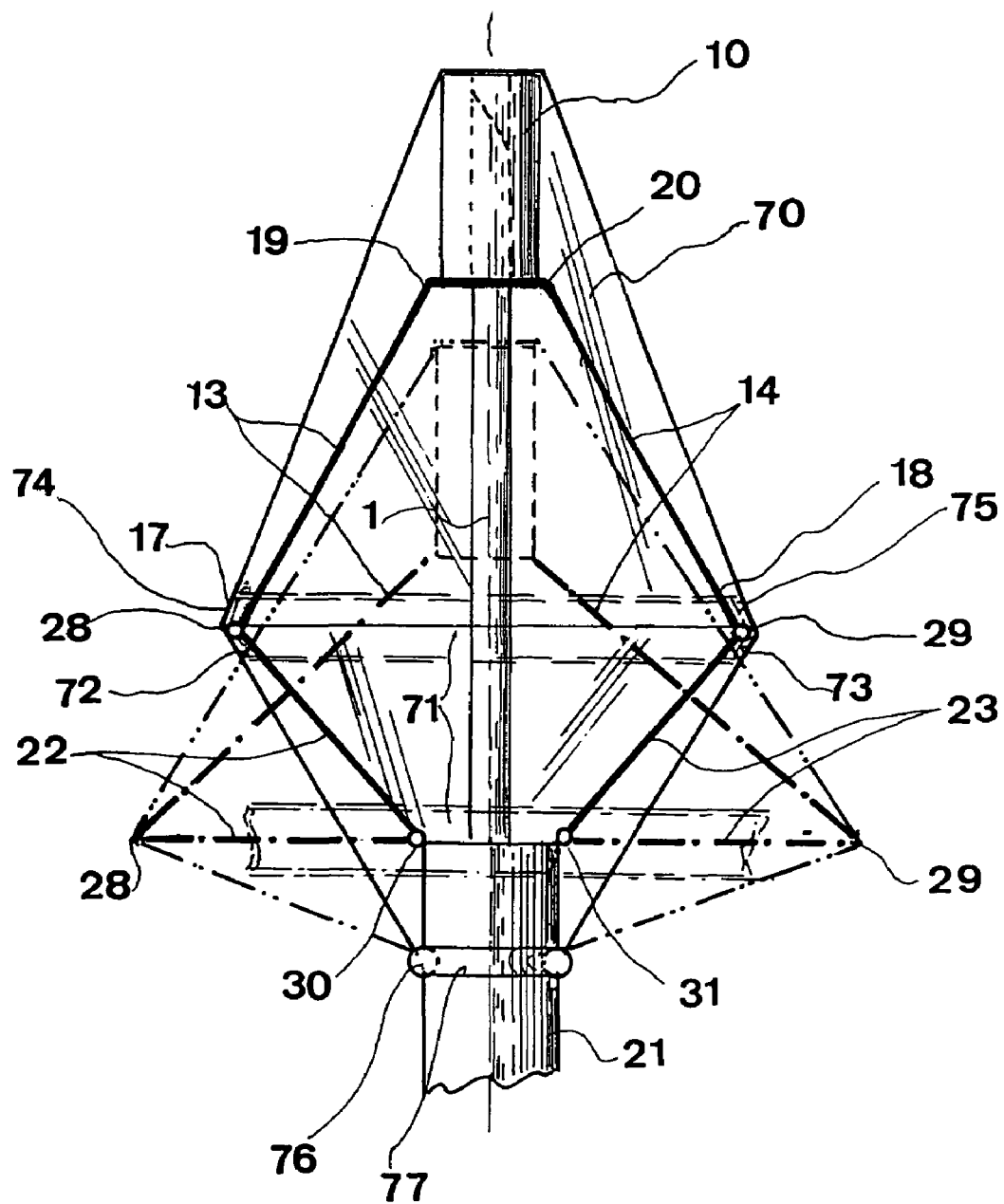
FIG. 6 is a diagram of an another embodiment of the device of the invention.
Figure 7:
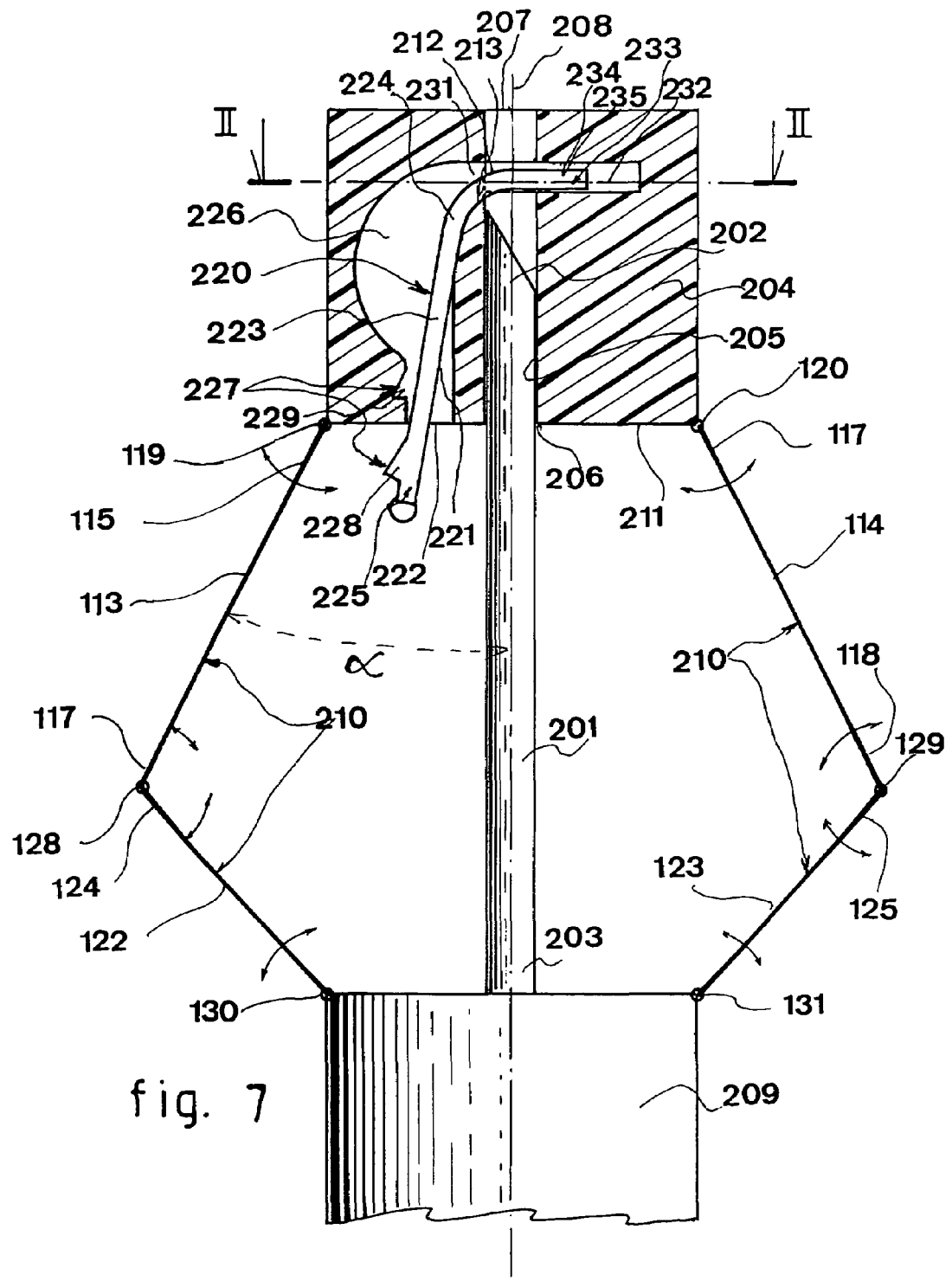
FIGS. 7 and 8 are two orthogonal diagrammatic section views of an another embodiment of the device of the invention, FIG. 7 being a section view on line I—I in FIG. 8 and FIG. 8 being a section view on line II—II in FIG. 7.
Figure 8:
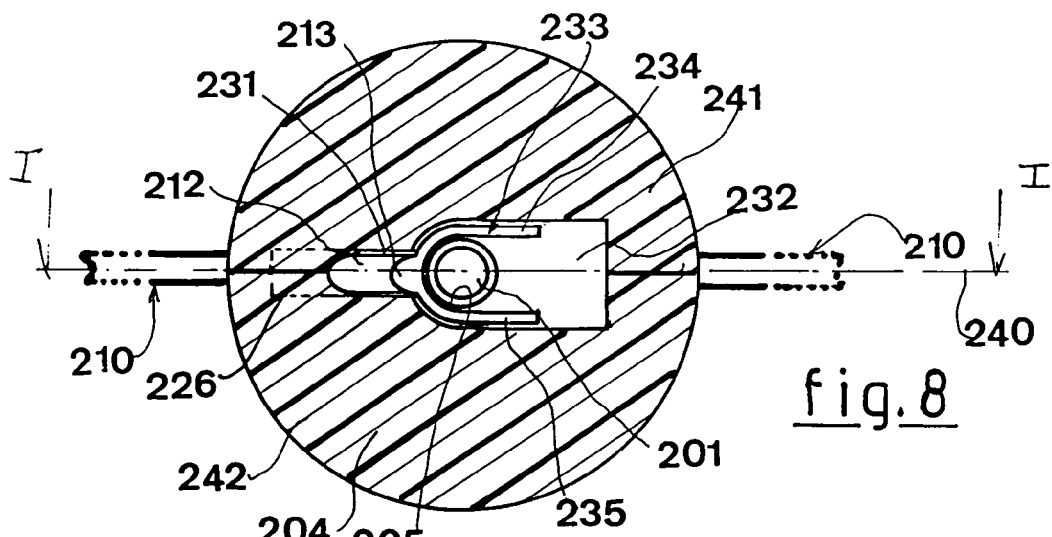
Figure 9:
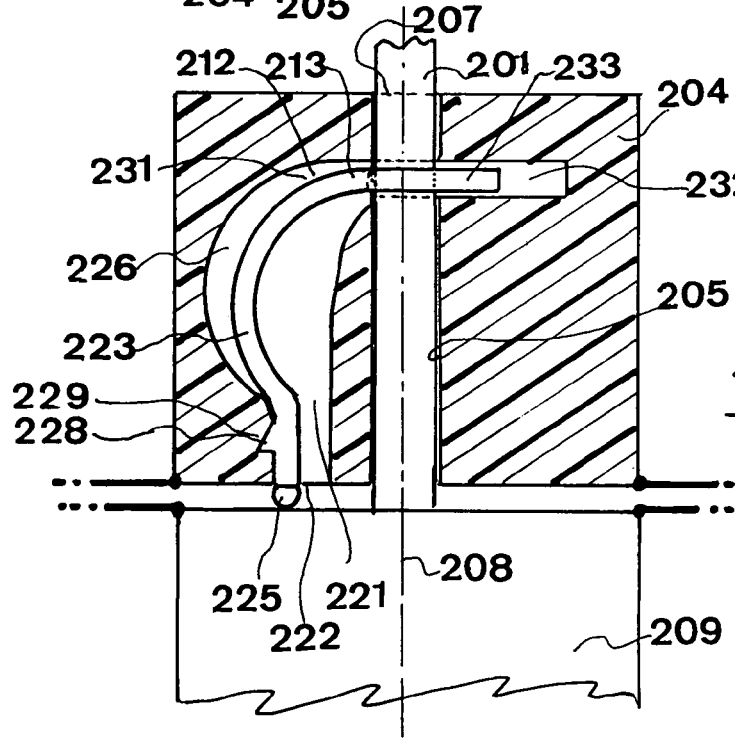
Figure 10:
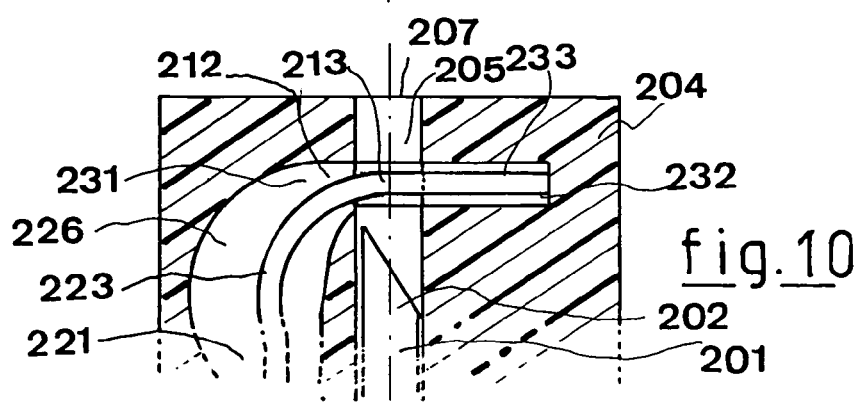

FIGS. 9 and 10 are fragmentary views of the device of FIGS. 7 and 8 shown in two respective configurations, FIG. 9 showing a portion of the device in an "intermediate" configuration corresponding to preparing to neutralize the needle, and FIG. 10 showing the same portion of the device in its configuration where the needle is completely neutralized, and FIGS. 11 and 12 are two embodiments of the base means as illustrated in FIGS. 1 to 10.

FIG. 1 is a theoretical diagram of a device of the invention for protecting and neutralizing a needle 1 for medical use or the like, the needle having a sharp end 2 and a base end 3, it being understood that this theoretical diagram could equally well be a diagrammatical representation of an embodiment of the device.

With reference to the diagram, the device comprises a sleeve 10 having a through bore 11 defined on a given axis 12, said through bore 11 being of a section that is not less than that of the needle to be protected so as to enable the sleeve to slide easily, advantageously over the entire length of the needle 1.

In this embodiment, the device has a link comprising first 15 and second 17 ends, said link having a defined length "$L_1$" between its two ends.

This link 13 associated with a point 39 of the sleeve 10 first resilient return hinge means 19 which connect the first end 15 of the link 13 to the sleeve 10, said first hinge means being mounted relative to the link in such a manner as to ensure that the link takes up a defined equilibrium position extending in a direction that makes an acute angle α relative to the axis 12 of the through bore so that, when the link is moved away from this equilibrium position under drive from any force, it tends automatically to return to said position as soon as the action of the force ceases.

The device also includes base means 21 suitable for receiving the base end 3 of the needle 1. These base means 21 may be of any type. For example, they may be constituted by a conically tapered end fitting, but clearly they can take up any other shape as a function of the nature and the use of the needle. These means can even be constituted by a portion of a syringe or the like.

These means 21 may also be constituted by a sheath or the like suitable for surrounding and engaging the base portion 3 of the needle to be protected 1. This is the embodiment shown in FIGS. 1 to 5.

In FIG. 1, the device also has a crank arm 22 defined between first and second ends 24 and 26. This crank arm 22 is of defined length "$I_1$" between its two ends 24 and 26, where the length "$I_1$" is no greater than the length "$L_1$" of the first link.

As shown diagrammatically in FIG. 1, the device finally includes first means 28 for mounting each of the first and second ends 24 and 26 of the crank arm 22 so that they can pivot freely respectively relative to the second end 17 of the link 13 and relative to a point 38 on the base means 21.

Figure 2:
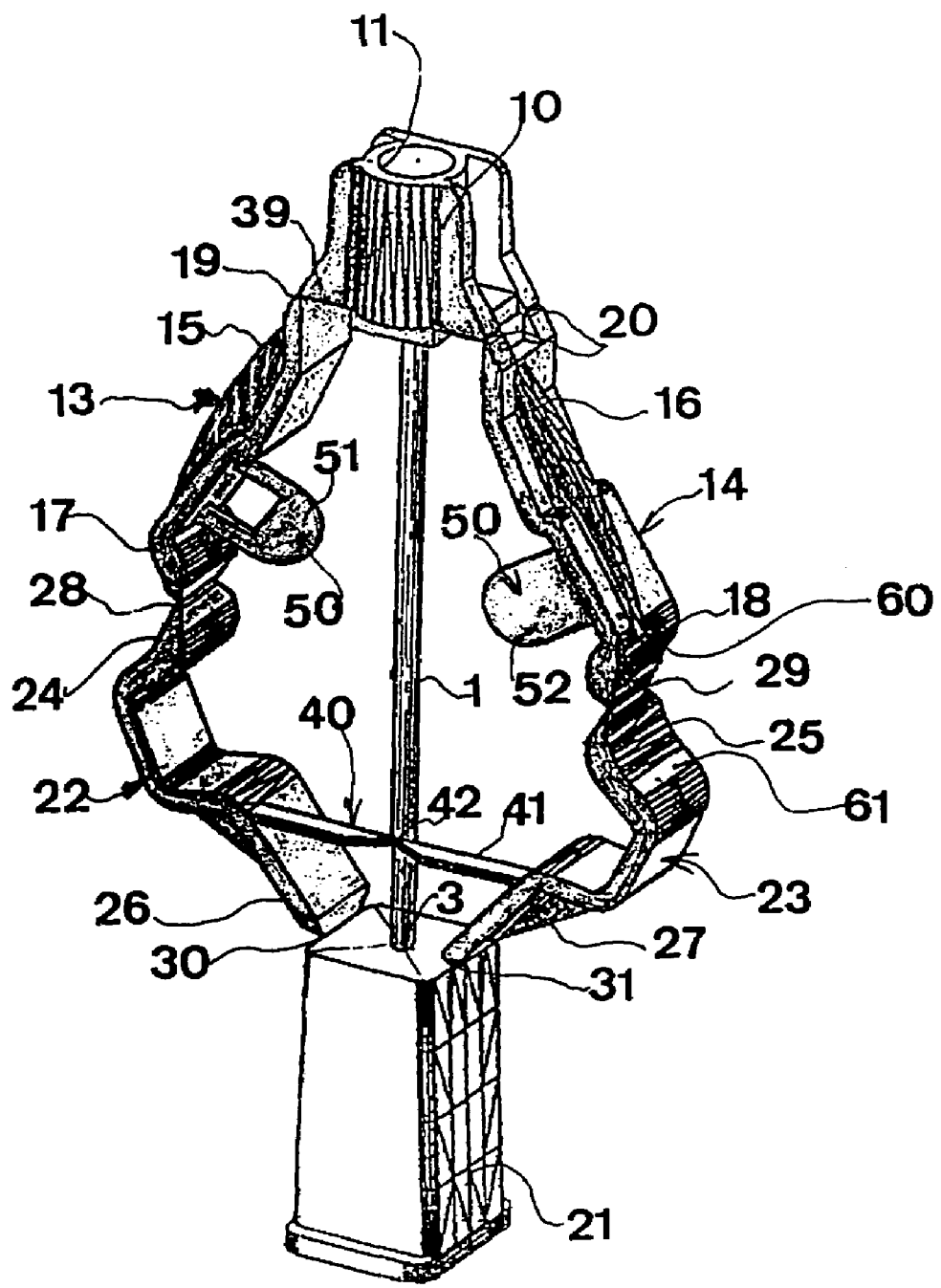
FIG. 2 is a perspective view of a preferred embodiment of the device of the invention.

The device as described above operates and is used as follows:

Firstly, it is assumed that the device is in the configuration (I) referred to as the "starting position" as shown in FIG. 1 in solid lines and as shown in FIGS. 2 and 3. In this position, the sharp end 2 of the needle is situated inside the through bore 11 made in the sleeve 10 and is thus protected therein.

In practice, the device can be associated with a needle 1 while the device is in this configuration (I), and then the resulting assembly can be sterilized and commercialized in conventional manner, e.g. in a sterile package or blister.

When the needle is to be used by nursing staff, the "protection device and needle" assembly is extracted from the packaging, and then the device is put into the configuration (II) referred to as the "in-use position" as shown in chain-dotted lines in FIG. 1 and as shown in FIG. 4.

To move the needle protection device from its starting position (I) to its in-use position (II), the user exerts, e.g. by hand, opposing forces on the sleeve 10 and on the base 21 so as to move the sleeve closer to the base, in sliding motion as represented by arrow 35.

During this movement, the resilient hinge 19 enables the link 13 initially to be subjected to first pivoting in a clockwise direction, as shown in FIG. 1, about the hinge point 39. This movement is imposed by the crank arm 22 pivoting counterclockwise about its free pivot point 30. When its free pivot point 28 passes through and moves below the plane 37 perpendicular to the axis 12 and containing the above-defined point 38 on the base, the return spring effect of the above-defined hinge 19 tends to cause the link 13 to be subjected to pivoting in the opposite direction, i.e. counterclockwise as shown in FIG. 1, thereby returning it towards its original position relative to the axis 12.

Under the action of this resilient return force which can be in addition to the opposing forces exerted between the sleeve 10 and the base 21, the link 13 thus drives the sleeve even more rapidly towards the base, and the device takes up its in-use position (II) shown in chain-dotted lines in FIG. 1.

In this configuration (II), the needle 1 is completely disengaged. It can then be used in conventional manner for the function for which it is designed, given that this function need not be described herein since the use of a needle is well known per se.

When the needle has been used, the user can push the sleeve 10 back towards the sharp end 2 of the needle tending to cause it to return to its starting position, with the sleeve 10 sliding along the needle 1 in the direction of arrow 36 until the sharp end 2 of the needle is situated inside the bore 11 and is covered by the sleeve 10.

The device can be moved manually from its in-use position (II) to its starting position (I) by pressing against the end 24 of the crank arm 22 relative to the base 21.

It is recalled that FIG. 1 is a diagram showing the principle of the device of the invention, and also showing a first embodiment thereof. In this embodiment, the device has only one link 13 and only one crank arm 22, and although it is completely functional, it is nevertheless advantageous to give the device a structure of the kind shown in FIGS. 2 to 5.

The embodiment of the device shown in FIGS. 2 to 5 is advantageous since its structure is symmetrical and thus balanced, thereby improving its operation compared with the operation of the embodiment shown in FIG. 1.

In the embodiment shown in FIGS. 2 to 5, and compared with the embodiment shown in FIG. 1, the device of the invention further includes: a second link 14 defined between first and second ends 16 and 18, said second link being of defined length "$L_2$" between its two ends; second resilient return hinge means 20 for connecting the first end 16 of the second link to the sleeve 10, the second hinge means being organized to cause the second link to take up a defined equilibrium position on a direction that makes an acute angle α with the axis of the through bore; a second crank arm 23 defined between first and second ends 25 and 27, the second crank arm being of defined length "$l_2$" between its two ends, the length "$l_2$" being no greater than the length "$L_2$" of the link; and second means 29, 31 for mounting the first and second ends of the second crank arm respectively to pivot freely on the second end of the second link 14 and on the base means 21.

In the advantageous embodiment shown, in order to obtain a device that is accurately symmetrical about the axis 12, the lengths "$L_1$" and "$L_2$" are substantially equal to a common value "L" and the lengths "$l_1$" and "$l_2$" are substantially equal to a common value "l".

In addition, in order to make the device easier to manufacture industrially and in order to make it as compact as possible, it is advantageous for the two links 13, 14 and for the two crank arms 22, 23 to lie substantially in the same plane and to form substantially a quadrilateral whose diagonals are substantially perpendicular, the diagonal connecting the vertices of the quadrilateral situated respectively at the sleeve 10 and at the base means 21 substantially coinciding with the axis 12 of the through bore 11.

It is also possible for the same material, e.g. a plastics material, to be used to make at least two of the following elements: sleeve 10; base means 21; link 13, 14; crank arm 22, 23; hinge means 19, 20; and freely pivoting mounting means 28, 29, 30, 31.

Nevertheless, it is particularly advantageous to make all of the component elements of the device out of said same material, thereby enabling it to be made single piece by the well known method of molding. Concerning this point, FIGS. 2 to 5 show, by way of example, the shape which can be given to each of the elements when made of a plastics material by the molding technique, and they also show reinforcing means for stiffening the links and the crank arms.

This method of manufacture also makes it possible to provide the hinge means 19, 20 and the freely pivoting mounting means 28, 29, 30, 31, directly and simultaneously with the other component elements of the device. In particular, the functions of the resilient return hinge means and of the freely pivoting mounting means can easily be obtained by giving an appropriate shape firstly to the portions of plastics material connecting the links 13, 14 to the sleeve, and secondly to the portions of plastics material connecting the crank arms 22, 23 to the links and to the base means 21.

Making resilient return hinges and freely pivoting hinges in this way by using the characteristics of the material and special shapes such as walls of reduced thickness, or the like, is well known to persons skilled in plastics, and is not described more fully herein.

To stiffen the device as a whole when it is in its starting position prior to first use, it is advantageous for it further to include relative rigid strut means 40 directly or indirectly interconnecting a link 13 and a crank arm 22.

In FIGS. 2 and 3, these strut means 40 shown for the case when the structure of the device is in the form of a quadrilateral. In this embodiment, the strut means 40 are constituted by a bar 41 or the like connected via its two ends to the two crank arms 22 and 24, and having a weak point 42, e.g. in its middle. In this case, the connection between the link 13 and the crank arm 22 is an indirect connection.

Nevertheless, in a configuration other than that shown, the bar 41 can connect a link to a crank arm. The person skilled in the art will select the configuration that is most suitable as a function of the use of the device and/or as a function of its method of manufacture. For example, it is possible to choose an embodiment of the bar 41 that connects the end 15 of the link 13 to the end 26 of the crank arm 22, or a bar that connects the sleeve 10 to the base 21.

In conventional manner, the weak point 42 makes it possible, under the effect of a given amount of force, to break the strut means such as the bar 41 at its weak point. This force can be obtained, e.g. by exerting a force directly on the two portions of the bar situated on either side of its weak point 41, or indirectly by causing the device to go from its starting position (I), FIG. 3, to its in-use position (II), FIG. 4.

This characteristic is advantageous since, as mentioned above, it makes it possible to stiffen the device while it is in its starting position (I), and also because it serves to inform any user of a needle provided with such a protection device whether there is any risk that the needle has already been used. An intact bar means that it is certain that the needle has not been used, while a broken bar indicates that it might already have been used, in which case, on safety grounds, it would be more prudent not to use it.

As mentioned above, once the needle has been used, it is possible to return the device to its starting position (I), FIG. 3, thereby at least hiding the sharp end of the needle. Nevertheless, when using only the structural elements as described above, there is a risk that the sharp end can inadvertently become disengaged again from the inside of the sleeve, and for the needle to be used again, for example.

Thus, it is advantageous for the device of the invention to further include snap-fastening means 50 directly or indirectly locking the link and the crank arm relative to each other in a given position, in which the sharp end of the needle can no longer move out from inside the sleeve. By way of example, this position is one which enables the device to take up a position (III) or "locking position" as shown in FIG. 5 and as represented by dashed lines in FIG. 1. In this locking position (III) of the device, the sharp end of the needle is held definitively inside the sleeve, thereby preventing any risk of injury or of reuse.

FIGS. 2 to 5 show an embodiment of the snap-fastening means 50 for locking the link and the crank arm relative to each other in a given position. These locking means 50 are constituted by two hooks 51 and 52 secured respectively to the two links 13 and 14, and which hook together when, under the action of pressure exerted on the two links, the links are moved to be very close to each other, as shown in FIG. 5.

The lengths of the sleeve 10, of the links, and of the crank arms are determined in such a manner that, when the protection device is in this locking position (III), the links and the crank arms are substantially in alignment and the sharp end 2 of the needle 1 lies inside the sleeve 10.

To achieve this result, it is necessary for the length "M" of the sleeve, the length "L" of the link 13 (or of the links 13 and 14), and the length "I" of the crank arm 22 (or of the crank arms 22 and 23) to be determined in such a manner that the sums L+I and L+I+M bracket the length "A" of the needle 1 that is to be protected as measured between its sharp end 2 and its base end 3, i.e. these lengths must satisfy the following relationship:

$$L+I<A<L+I+M$$

One embodiment of the locking means 50 is described above, however it is clear that other types can exist, for example pawls or the like positioned on the two curved portions 60 and 61 adjacent to the freely pivoting mounting means 28 and 29, to act respectively between the links 13, 15 and the crank arms 22, 23 and which face one another when the device is in its locked position (III). These pawls are not shown in order to simplify the drawings. For example they may be constituted by two projections situated on the two curved portions 60 and 61 respectively and including, for example, curved ends shaped to pass over each other when the links and the crank arms are brought into alignment, and shaped so as to make it impossible to separate them by moving in the opposite direction.

These snap-fastening locking means may also be constituted by two tamperproof male-female engagement elements, having complementary barbs respectively on their outer walls and on their inner walls, which barbs can move relative to each other only in one direction of displacement of the male element in the female element. Barbs of this type are well known per se to the persons skilled in the art and are therefore not described in greater detail herein.

The FIG. 6 is a diagram of an another embodiment of the device of the invention.

As shown in FIG. 6, the device of the invention for protecting and neutralizing a needle 1 for medical use or the like includes, in addition to the essential characteristics described above with reference to FIGS. 1 to 5, a casing 70 made of a resilient material surrounding, under tension, the assembly constituted by the sleeve 10, the first and second links 13, 14, the first and second hinge means 19, 20, the first and second crank arms 22, 23, the first and second means 28, 29, 30, 31 for mounting each of the first and second ends of the first and second crank arms respectively on the second ends 17, 18 of the first and second links 13, 14 and on the base means 21, and at least a portion of the base means 21.

The resilient material from which the casing 70 is made is transparent, or substantially transparent, so that users of the device can see through the wall of the casing and therefore see, in particular, the needle and any indications that may possibly be carried by the various elements mentioned above.

The needle 1 is thus protected from the outside environment, as with a "blister" type casing. However, unlike a prior art blister which must be removed before the needle can be used, the casing 70 does not have to be removed. When the needle moves out from the sleeve as explained above with reference to FIGS. 1 to 5, it passes through the wall of the casing 70 without difficulty and, as the material from which the casing is made is also resilient, said wall fits tightly around the needle to constitute a sealed passage.

The device may further includes sachet 71 the like disposed inside the casing 70, said sachet being made of a non-stretch material and containing a given substance.

The sachet is also capable of tearing under a given traction, and means 72, 73 are provided for securing two of its points 74, 75 with two substantially opposite points of the inside wall of the casing 70 that are advantageously situated substantially facing the first and second means 28, 29 for mounting the first ends of the first and second crank arms to pivot freely on the second ends of the first and second links.

By way of example, the substance contained in the sachet 71 presents at least one of the following properties: being suitable for absorbing at least a portion of visible light, being suitable for hardening, being suitable for sterilizing.

In this way, when the needle 1 is used for the first time as explained above, and the two hinges 28, 29 move away from each other when the sleeve descends along the needle, the two points 74, 75 also move away from each other, pulling the sachet and causing it to tear. The substance that it contains thus spreads into the casing 70.

However, the sachet 71 tears only when the sharp end 2 of the needle 1 has already passed through the wall of the casing and is ready to be used for an injection.

It should be noted that the substance spread inside the casing cannot escape therefrom, since, as mentioned above, the wall of the envelope where perforated by the needle fits tightly around the needle and constitutes a sealed passage.

Thus, when the substance is suitable for absorbing at least a portion of visible light, i.e. when it is colored, it is visible to the human eye and, if the colored substance has filled the chamber of the casing, then the users of the device are informed of the fact that the needle might already have been used.

When the substance is suitable for hardening, once the needle has been used and the entire device has been returned to its original configuration after injection, the links, the crank arms, the sleeve, and the base become embedded in the substance and secured to one another. It is therefore no longer possible to reuse the needle.

Finally, when the substance is suitable for sterilizing objects, once the device has been returned to its original position after the needle has been used, the needle is soaked in the substance that has spread inside the casing and is therefore sterilized by said substance, thereby avoiding contamination if ever a person should be pricked with the sharp end of a needle which has inadvertently come out of the casing. FIGS. 7 to 10 show an another embodiment of the device of the invention for protecting and neutralizing a needle for medical use or the like.

This device, according the FIGS. 7 and 8, comprises a sleeve 204 with a through bore 205, the through bore having first and second outlets 206 and 207, said through bore being defined on a given axis 208 and being of cross-section that is not less than that of the needle 201 so that the needle can slide through said through bore.

The device also has both a base 209 secured to the base end 203 of the needle 201, said base serving in conventional manner to connect the needle to a syringe, and resilient link means 210 connecting the sleeve 204 to the base 209, these resilient link means enabling the sleeve 204 to slide along the needle 201, with the needle penetrating the through bore 205 of the sleeve via its first outlet 206 so that the sleeve is suitable for taking up two extreme positions: a first position in which the sleeve surrounds the sharp end 202 of the needle, this sharp end being situated at a given distance from the second outlet 207 of the through bore 205; and a second position in which the face 211 of the sleeve 204 that includes the first outlet 206 of the through bore is located close to the base 209.

These resilient link means 210 are constituted, for example, by: two links 113 and 114 each having respective first and second ends 115, 116–117, 118, said links being of a defined length "L" between their two ends; first resilient return hinge means 119, 120 for connecting the first ends 115, 116 of the two links to the sleeve 204, said first hinge means being organized so that the first two links take up a defined equilibrium position on a direction that makes an acute angle α relative to the axis of the through bore; two crank arms 122, 123, said crank arms being respectively defined between first and second ends 124, 125–126, 127 and being of defined length "I" between their two ends, where the length "I" of the crank arms is no greater than the length "L" of the links; and first means 128, 129, 130, 131 for mounting each of the first and second ends of the two crank arms respectively to pivot freely relative to the second ends 117, 118 of the two links, and relative to the base 221. Advantageously, the two links and the two crank arms are situated substantially in the same plane and form substantially a quadrilateral whose diagonals are substantially perpendicular. In addition, it is advantageous for the length "L" of the links and for the length "I" of the crank arms to be determined in such a manner that the sums L+I and L+I+M, where "M" represents the length of the sleeve 204, bracket the length of the needle 201 to be protected as measured between its sharp end 202 and its base end 203.

The device also has both a first channel portion 212 formed in the sleeve 204 and intersecting the through bore 205 in its portion lying between its second outlet 207 and the sharp end 202 of the needle 201 when the sleeve 204 is in its first position, and shutter 213 slidably mounted in said first channel portion 212, said shutter being suitable for taking up a first position and a second position: the first position being one in which it is not situated in the through bore 205; and the second position being one in which it is situated in the through bore. The device also has means 220 for applying a pressure force on the shutter 213 when the sleeve 204 comes close to the base 209 on the sleeve going from its first position to its second position.

In a preferred embodiment, these means 220 comprise a second channel portion 221 formed in the sleeve 204 in continuity with said first channel portion and opening out via an outlet orifice 222 in the face 211 of the sleeve that includes the first outlet 206 of the through bore 205, associated with a flexible rod 223 that is preformed into an arcurate shape and that is slidably mounted in said second portion of the second channel portion 221. A first end 224 of the two ends of the flexible rod is associated with the shutter 213, while its other end 225 initially emerges from the outlet orifice 222 of the second channel portion by an amount that is not less than the distance which the shutter 213 needs to travel in order to pass from its first position to its second position.

These means 220 also include a release cavity 226 adjacent to the second channel portion 221 and in communication with said second channel portion, the shape of the release cavity also being defined so that, when the shutter 213 is held in its first position, the flexible rod 223 can deform in bending like a strung bow and can penetrate laterally into said release cavity 226 when the face 211 of the sleeve having said first outlet 206 of the through bore 205 comes close to the base 209.

The device also has means 227 for locking the second end 225 of the flexible rod 223 in position when the rod is retracted into the second channel portion 221. These means 227 are constituted by at least one barb 228 secured to the flexible rod 223 and a housing 229 complementary to the barb 228 formed in the wall of the second channel portion 221 so as to engage the barb in a male-female type manner.

In an advantageous embodiment as shown in the figures, the first channel portion 212 comprises at least first and second parts 231 and 232 disposed on either side of the through bore 205, the first part 231 of the first channel portion being in line with the second channel portion 221, the shutter 213 being contained completely within said first part 231 of the first channel portion 212 when it is in its first position.

The device also includes a substantially U-shaped fork 233 secured to the shutter 213, the two limbs 234 and 235 of the fork being spaced apart from each other by a distance that is not less than the diameter of the needle 201, and said fork 233 being shaped in such a manner that, when the shutter 213 is in its first position, the space 236 defined between the two limbs 234 and 235 lies on the axis 208 of the through bore 205, with the two limbs 234 and 235 extending at least to some extent into the second part 232 of the first channel portion.

In an advantageous embodiment, the flexible rod 223, the shutter 213, and the fork 233 are made as a single piece, e.g. of molded plastics material.

With the above-defined structure, it is advantageous for the axes of the two channel portions 212 and 221 to be contained in a common plane 240 which also contains the axis 208 of the through bore 205. In which case, the sleeve 204 can be made as two half-shells 241 and 242 organized to be assembled together on the plane 240 which contains the channel portions 212 and 221, thus making it possible to use plastics material, for example, to make the sleeve by using the molding technique with molds that are very simple to make. To obtain the device, it suffices to place the single "flexible rod and shutter and fork" piece in the two channel portions and to enclose it by placing the two half-shells one against the other, after which the half-shells can be bonded together, e.g. by laser beam.

The above-described device as regarding FIGS. 7 and 8, operates and is used as follows:

It is firstly stated that the needle is present in the device in a configuration of the kind shown in FIGS. 7 and 8.

In this configuration, the shutter 213 is entirely contained in the first part 231 of the first channel portion 212, with the fork 233 allowing the needle 201 to pass through, and with the end 225 of the flexible rod 223 emerging via the orifice 222 of the second channel portion 221, the sharp end 202 of the needle being properly protected since it is surrounded by the sleeve 204.

When a user seeks to perform an injection using such a needle, the user slides the sleeve 204 towards the base 209. During this movement, the two links 113 and 114 are caused to pivot respectively clockwise and counterclockwise while the two crank arms 122 and 123 are caused to pivot respectively counterclockwise and clockwise. The needle comes out from the through bore 205 via its outlet 207, passing between the two limbs 234 and 235 of the fork 233.

When the sleeve 204 comes close to the base 209, the end 225 of the rod 223 comes into abutment against the base. Since the needle is in position between the two limbs of the fork, the shutter 213 is held in position, and when its end 225 is pushed into the second channel portion 221, the rod 223 folds into an arcuate bow-shape, penetrating into the release cavity 226. When the end 225 is almost fully retracted into the second channel portion 221, the barb 228 catches in the housing 229. At this stage, the device takes up the configuration shown in FIG. 9.

After the injection has been completed, the user causes the sleeve 204 to slide back along the needle until it returns to the position shown in FIG. 7. Since the end 225 of the prestressed rod 223 is held in place by mutual engagement between the barb and the housing, the rod applies thrust on the shutter 213. So long as the needle is to be found between the two limbs 234 and 235 of the fork, the shutter remains in its starting position (FIG. 9). However, when the sleeve returns to its starting position relative to the base 209, the sharp end 202 of the needle is disengaged from the fork 233 so the shutter is subjected to drive from the thrust force exerted by the prestressed rod 223, thereby causing the shutter to move into the first channel portion 212 so as to shut off the through bore 205. This translation movement of the shutter is guided in particular by the two limbs 234 and 235 of the fork which already extend into the second part 232 of the first channel portion 212. The device then takes up the configuration shown in FIG. 10.

It is then impossible for a user to use the needle 201 again since the user can no longer cause the sleeve to slide towards the base, given that the sharp end of the needle comes automatically into abutment against the shutter 213 which prevents it from moving out of the through bore 205.

FIGS. 11 and 12 show two particularly advantageous embodiments of the base means 21 or 209 before mentioned.

In these two embodiments, the base means 21 or 209 comprise two first and second rings 301, 302 (FIG. 11), 311, 312 (FIG. 12), with the first ring 301, 311 receiving the low end 3, 203 of the needle, and means 320 for connecting the two rings between them by weakpoints.

Moreover, in one possible embodiment, each of the two rings comprises an opening 321, 322, the two openings being realized in order to form, when the two rings are connected between them, the female part of a male-female jointing, able to cooperate with the complementary male part 323 constituted by an end-part located at the end of the cylindrical body 324 of a syringe 325.

In a preferential embodiment, as that which is illustrated on FIG. 12, the total depth of these two openings when the two rings are connected between them, is lower than the height of end-part 323.

It is as an advantage that the base means comprises a not-withdrawal ring 330 located on wall 331 of at least one of the two openings.

When the base means is carried out as described compared to FIG. 11 or FIG. 12, the device according to the invention brings an even greater safety when using the needles of medical use.

Indeed, in the case of the embodiment of the base means according to FIG. 11, it is advantageous to give to the second ring 302 a length higher than the height of end-part 323, in order not to allow the jointing of this end-part with the first ring 301. Consequently, if the device comprises this second ring 302, it is certain that the needle has not been used to carry out an injection. If the device does not comprise any more this second ring 302, it is extremely probable that the needle has been used and it is thus preferable not to use it again.

In the case of the embodiment of the base means according to FIG. 12, the end-part 323 can be plugged in force in openings 321, 322 and, to remove it, it is necessary to exert on it a relatively strong traction which involves a rupture of the weak points and a dissociation of the two rings 311, 312, with the ring 312 remaining plugged in the end-part. The fixing of the second ring 312 on end-part 323 may be reinforced by the presence of the not-withdrawal ring 330 on the wall 331 of this second ring.

What is claimed is:

1. A device for protecting a needle for medical use or the like, the needle having a sharp end and a base end, comprising:

a sleeve having a through bore defined on a given axis, said through bore being of a section that is not less than that of the needle to be protected;

a first link having first and second ends, said link being of a length "L1" defined between said two ends, wherein the first link is able to take at least three positions when the needle is positioned vertically upright with the sharp end of the needle above the base end of the needle, the three positions being an equilibrium starting position, an equilibrium in use position, and a locked position;

a first resilient return hinge means for connecting the first end of the first link to the sleeve, the resiliency of said first hinge means allowing said first link to takes up one or the equilibrium in use position and the equilibrium starting position, wherein the link makes an acute angle (ÿ) with respect to the axis of the through bore, when no force is applied to the link, and the needle is positioned vertically upright with the sharp end of the needle above the base end of the needle;

a base means suitable for receiving the base end of the needle to be protected;

a first crank arm, said first crank arm being defined between first and second ends, said crank arm being of a length "I1" defined between its two ends, the length "I1" of the first crank arm being no greater than the length "L1" of the first link; and first means for mounting each of said first and second ends of the first crank arm to pivot freely respectively on the second end of the first link and on the base means:

a second link having first and second ends said second link being of a length "L2" defined between said two ends;

second resilient return hinge means for connecting the first end of the second link to the sleeve, said second hinge means being organized so that said second link takes up a defined equilibrium position on a direction that makes an acute angle (ÿ') with the axis of the through bore;

a second crank arm, said second crank arm being defined between first and second ends, said second crank arm being of a length "I2" defined between its two ends, the length "I2" of the second crank arm being no greater than the length "L2" of the second link; and second means for mounting each of said first and second ends of the second crank arm to pivot freely respectively on the second end of the second link and on the base means.

2. A device according to claim 1, further including strut means connecting said first link to said first crank arm when they are in a first position, said strut means including a weak point making it possible, on application of a given force, to break said strut means at said weak point.

3. A device for protecting and neutralizing a needle for medical use or the like the needle having a sharp end and a base end, the device comprising:

a sleeve having a through bore, said through bore having first and second outlets, said through bore being defined on a given axis and having a cross-section that is not less than that of the needle, the needle being suitable for sliding through said bore;

a base secured to the base end of the needle; and resilient link means connecting the sleeve to the base, said resilient link means enabling the sleeve to slide along the needle, the needle passing through the bore of the sleeve via the first outlet thereof, said sleeve being suitable for taking up two extreme positions;

a first sleeve position in which the sleeve surrounds the sharp end of the needle, said sharp end being situated at a given distance from the second outlet of the through bore; and a second sleeve position in which the face of the sleeve that includes the first outlet of the through bore is positioned adjacent to the base; said resilient link means comprising at least:

a first link having first and second ends, said link being or a length "L1" defined between said two ends;

first resilient return hinge means for connecting the first end of the first link to the sleeve, said first hinge means being organized so that said first link takes up a defined equilibrium position on a direction that makes an acute angle (ÿ) with the axis of the through bore;

a first crank arm, said first crank arm being defined between first and second ends, said crank arm being of a length "I1" defined between its two ends the length "I1" of the first crank arm being no greater than the length "L1" of the first link; and first means for mounting each of said first and second ends of the first crank arm to pivot freely respectively on the second end of the first link and on the base means, wherein said device further comprises:

a first channel portion made in the sleeve and intersecting the through bore in a portion lying between its second outlet and the sharp end of the needle when the sleeve is in the first sleeve position;

a shutter slidably mounted in the first channel portion, said shutter being suitable for taking up a first shutter position and a second shutter position, the first shutter position being one in which it is not situated in the through bore, and means for applying thrust on said shutter when the sleeve comes close to the base on passing from the first shutter position to the second shutter position.

4. A device according to claim 3, wherein the means for applying thrust on said shutter when the sleeve comes close to the base on passing from the first sleeve position to the second sleeve position are constituted by;

a second channel portion made in the sleeve in continuity with the first channel portion and opening out via an outlet orifice in the same face of the sleeve as has the first outlet of the through bore;

a flexible rod preformed into an arcuate bow shape and slidably mounted in said second channel portion in such a manner that a first end thereof is associated with the shutter, and a second end thereof emerges from the outlet orifice of the second channel portion by an amount that is not less than the distance the shutter needs to travel in order to pass from the first shutter position to the second shutter position; and a release cavity adjacent the second channel portion and in communication with said second channel portion, the release cavity being designed so that, when the shutter is held in the first shutter position, the flexible rod can deform in bending to penetrate laterally into said release cavity when the face of the sleeve having the first outlet of the through bore comes close to the base.

5. A device according to claim 4 further including means for locking the position of the second end of the flexible rod when said rod is caused to enter into the second channel portion.

6. A device according to claim 5 wherein the means for locking the position of the second end of the flexible rod when it is retracted into the second channel portion is constituted by at least one barb secured to the flexible rod and a housing complementary to the barb formed in a wall of the second channel portion.

7. A device according to claim 4 wherein the first channel portion has at least a first part and a second part formed on either side or the through bore, the first part of the first channel portion being in line with the second channel portion, the shutter being contained completely within said first part of the first channel portion when the shutter is in the first shutter position, and by the fact that the device further includes a substantially U-shaped fork secured to the shutter and having two limbs, the two limbs of the fork being spaced apart from each other by a distance of not less than the diameter of the needle, said fork being shaped in such a manner that when the shutter is in the first shutter position, the space defined between the two limbs thereof is situated on the axis of the through bore and the two limbs extend at least in part into the second part of the first channel portion.

8. A device according to claim 7 wherein the flexible rod, the shutter, and the fork are made as a single piece.

9. A device according to claim 8 wherein said piece is made of plastics material by molding.

10. A device according to claim 4 wherein the two channel portions are contained in a plane that also contains the axis of the through bore, the sleeve being made as two half-shells organized to be assembled together about said plane containing the two channel portions.

11. A device according to claim 1, wherein the base means comprises two first and second rings, the first ring receiving the base end of the needle, and means for connecting said two rings between them by weak points.

12. A device according to claim 11 wherein the two rings respectively include two openings, the two openings being realized to form, when the two rings are connected between them, a female part of a male-female joining able to cooperate with the complementary male part constituted by an end-part of a syringe, the total depth of these two openings, when the two rings are connected between them, being lower than the height of the end-part of the syringe.

13. A device according to claim 11 further including a not-withdrawal ring located on a wall of said second ring.

14. A device according to claim 1, wherein the lengths "L1" and "L2" are substantially equal to common value "L" and that the lengths "I1" and "I2" are substantially equal to a common value "1".

15. A device according to claim 1, wherein the first and second links and the first and second crank arms are situated substantially in a common plane and form substantially a quadrilateral whose diagonals are substantially perpendicular, the diagonal interconnecting the vertices of the quadrilateral situated respectively at the sleeve and at the base means coinciding substantially with the axis of the through bore.

16. A device according to claim 1, wherein at least two of the following elements are made of the same material: sleeve; base means; link; crank arm; hinge means; and freely pivoting mounting means.

17. A device according to claim 16 wherein said at least two elements are made by molding.

18. A device according to claim 17 wherein the material is a plastics material.

19. A device according to claim 1, wherein the length "L1" of the link and the length "I1" of the crank arm are determined in such a manner than the sum L1+I1 and the sun L1+I1+M1, where "M" represents the length of the sleeve, bracket the length "A" of the needle to be protected as measured between the sharp end and the base end.

20. A device according to claim 1, further including a casing made of a resilient material surrounding under tension the assembly constituted by the sleeve, the first and second links, the first and second hinge means, the first and second crank arms, the first and second means for mounting the first and second ends of the first and second crank arms to pivot respectively on the second ends of the first and second links and on the base means, and at least a portion of the base means.

21. A device according to claim 20 wherein the resilient material from which the casing is made is transparent.

22. A device according to claim 20 further including a sachet made of a non-stretch material, the sachet containing a given substance and being capable of tearing under a given traction, and means for securing the sachet and the casing substantially at two opposite points of the inside wall of the casing, the two said points being situated substantially facing the first means for mounting the first ends of the first and second crank arms to pivot freely on the second ends of the first and second links.

23. A device according to claim 22, wherein the substance contained in the sachet presents at least one of the following properties: being suitable for absorbing at least a portion of visible light, being suitable for hardening, being suitable for sterilizing.

24. A device according to claim 1, further including, for neutralizing said needle, snap-fastening means to lock said link and said crank arm relative to each other in a second given position.

* * * * *